United States Patent [19]

Bortnick

[11] Patent Number: 4,481,410
[45] Date of Patent: Nov. 6, 1984

[54] FAIL SAFE STERILIZING APPARATUS AND A CIRCUIT THEREFOR

[76] Inventor: Kenneth A. Bortnick, Rte. 2 Box 154, Parsonsburg, Md. 21849

[21] Appl. No.: 536,316

[22] Filed: Sep. 27, 1983

[51] Int. Cl.³ .............................................. F27D 11/02
[52] U.S. Cl. .................................... 219/521; 219/386; 219/441; 219/452; 219/524; 422/307
[58] Field of Search ............... 219/386, 387, 437, 438, 219/439, 444, 451, 452, 462, 456, 521, 524, 525, 536; 422/105, 116, 300, 307; 126/275 E; 204/186, 302; 351/160 R, 247

[56] References Cited

U.S. PATENT DOCUMENTS

| | | | |
|---|---|---|---|
| 1,157,731 | 10/1915 | Sprenger | 219/452 |
| 3,440,406 | 4/1969 | Sege, Jr. | 219/452 X |
| 3,586,824 | 6/1971 | Barney | 219/452 |
| 3,746,837 | 7/1973 | Frey et al. | 219/387 |
| 3,801,278 | 4/1974 | Wagner et al. | 219/521 X |
| 3,983,362 | 9/1976 | Hoogesteger et al. | 219/521 |
| 4,044,226 | 8/1977 | Kadlecik et al. | 219/521 |
| 4,379,965 | 4/1983 | Dounce et al. | 219/521 |

Primary Examiner—Volodymyr Y. Mayewsky
Attorney, Agent, or Firm—Shlesinger, Arkwright, Garvey & Fado

[57] ABSTRACT

A fail safe sterilizing apparatus for simultaneously sterilizing lenses contained in a lens case and a bottle of rinse solution comprising a housing having a lid displaceable between an open position and a closed position; a first heat member displaceably mounted in said housing and including a first recess for receiving a first container therein; a second heat member displaceably mounted in said housing and including a second recess for receiving a second container therein; said first and second heat members being displaced when said first and second containers are positioned in said first and second recesses and said lid is in said closed position; switch means operable only when said first and second heat members have been displaced for permitting energizing of said first and second heat members; and, control means operably associated with said switch means for simultaneously energizing said first and second heat members is disclosed.

18 Claims, 4 Drawing Figures

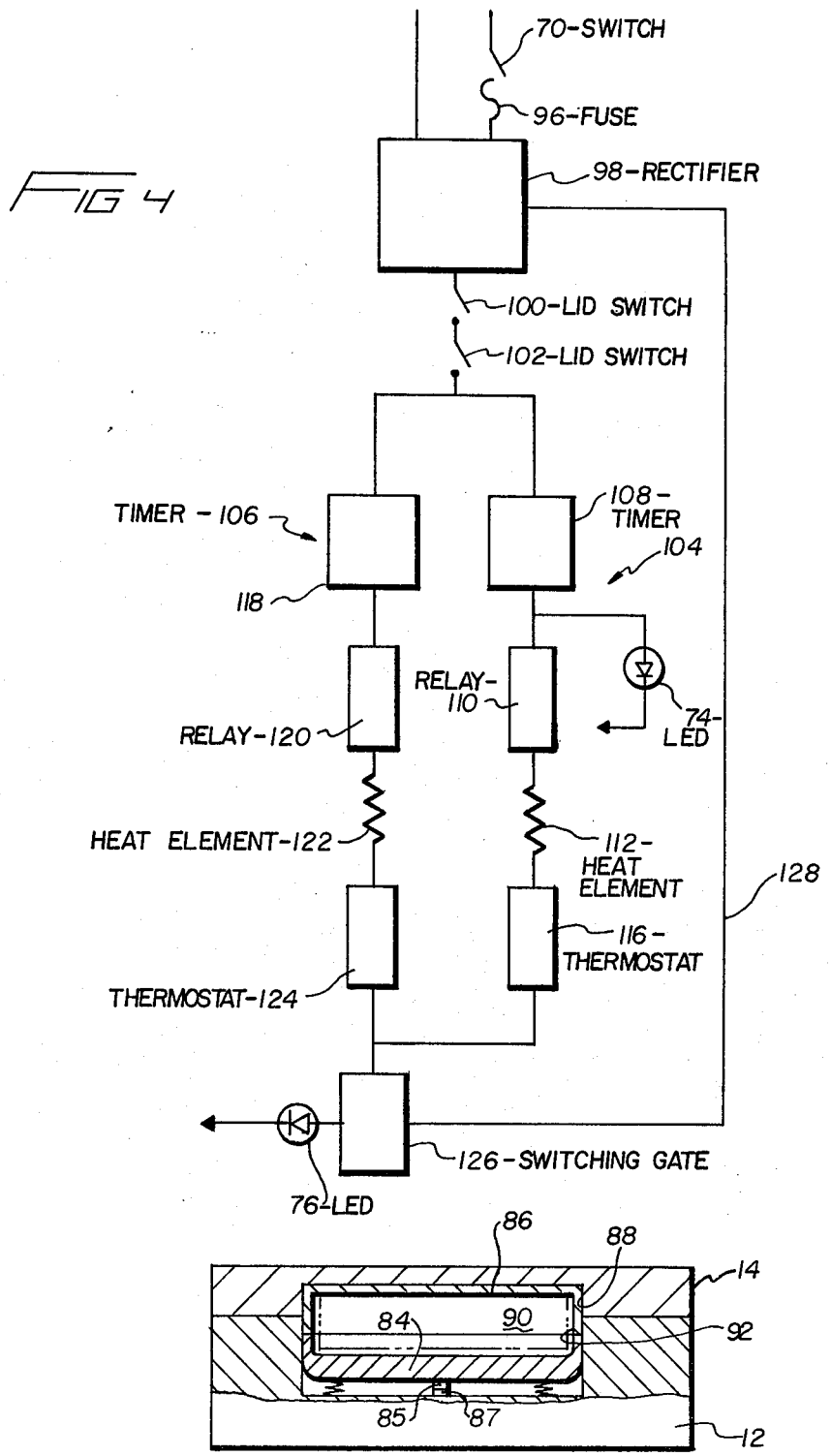

FAIL SAFE STERILIZING APPARATUS AND A CIRCUIT THEREFOR

BACKGROUND OF THE INVENTION

Hydrophilic contact lenses, i. e. soft contact lenses, have been commercially available for some time. Proper care of these lenses requires that they be disinfected, preferably daily, and that a rinse solution be applied to the lenses prior to insertion in the eye. It is important that the rinse solution, which is also used during the disinfection operation, be sterile so as to prevent ocular infection.

Non-preserved saline solutions were originally used and were made up daily from salt tablets and distilled water. Distilled water was necessary as the lenses are water absorbent and could pick up minerals or other contaminants in the water. Distilled water is not, however, sterile and the risk of ocular infection existed. Attempts to use preserved saline solutions suffered from the disadvantages that a number of patients were sensitive to the preservatives used and the cost of the preserved saline solutions was markedly higher than the patient prepared non-preserved saline solutions. Attempts to use unit dose containers of non-preserved saline solution were not effective as they were prohibitively expensive.

Prior art heat kits, of which Hoogesteger et al, U.S. Pat. No. 3,983,362, is a good example, provided a heat kit for sterilizing the contact lenses while held in a lens case. The lens case included two receptacles into which the lenses were placed along with a pre-measured amount of saline solution. The heat kit would then be operated to heat the contact lenses contained in the lens case to a pre-determined temperature for a pre-determined length of time, that is, until the lenses were sterilized. Hoogesteger did not, however, provide a means for sterilizing the rinse solution which is usually contained in a separate rinse solution bottle. Consequently, patients frequently applied non-sterile rinse solution to the lenses prior to insertion in the eye with the result of a greatly increased risk of ocular infection.

Wagner et al, U.S. Pat. No. 3,801,278, discloses a sterilizing apparatus for hydrophilic contact lenses having dual sterilizing compartments. Each of the compartments has its own heating element and a thermostat control but with a single timer controlling operation of both compartments. One of the compartments is used to disinfect a number of contact lenses, each pair of lenses being held in a separate lens container case, and the other compartment is used to sterilize a large quantity of saline solution contained in a bottle. The apparatus of Wagner is not, however, designed for use by the ordinary wearer of contact lenses but is, instead, designed for use by an optometrist or other eye care practitioner. Additionally, the duration of the sterilization process in Wagner is independent of the actual process needs of both the rinse bottle and the lens cases. Consequently, use of the Wagner device by a patient could result in under-sterilization of one of the containers with the risk therefore of ocular infection.

In view of the above noted disadvantages of prior art heat kits, a new and unique means for insuring the fail safe sterilization of a contact lens case containing a pair of contact lenses as well as a bottle of rinse solution is necessary. The present invention discloses and claims a novel apparatus for insuring patient compliance by requiring that both the contact lens case as well as the rinse solution bottle be positioned in their separate independently controlled heating compartments prior to initiating operation of the heat kit. Should one of the compartments not be filled, then the apparatus will not operate.

OBJECTS AND SUMMARY OF THE INVENTION

It is a primary object of the disclosed invention to provide a single unit dual sterilizing compartment fail safe apparatus for simultaneously sterilizing a bottle of saline solution and a pair of soft contact lenses contained in a lens case.

It is an additional object of the disclosed invention to insure patient compliance with proper safety procedures required for the use and care of soft contact lenses and the rinse saline solution.

Yet an additional object of the disclosed invention is to provide a fail safe sterilizing apparatus with the compartments being configured to conform to the shape of the soft contact lens carrying case and to the shape of the rinse solution bottle.

Still a further object of the disclosed invention is to provide a fail safe sterilizing apparatus which prohibits operation of the sterilizing apparatus should either or both of the sterilizing compartments fail to be occupied by its appropriate container.

Still another object of the disclosed invention is to provide a fail safe sterilizing apparatus in which the sterilizing compartments cooperate with the sterilizer lid in order to insure cooperation with sterilizing compartment switches.

Yet a further object of the disclosed invention is to provide a fail safe sterilizing apparatus having electrically operable indicia for indicating operation of the apparatus and also to indicate that the apparatus has cooled sufficiently to permit the lenses to be worn and the rinse solution to be used.

Yet an additional object of the disclosed invention is to provide a fail safe sterilizing apparatus which is compact and manufactured from a minimum of parts.

Yet still a further object of the disclosed invention is to provide a fail safe sterilizing apparatus having separate timers for each of the sterilizing compartments.

Yet another object of the disclosed invention is to provide a fail safe sterilizing apparatus having cooperative thermostats adapted for energizing electrically operable indicia to indicate to the user that the sterilizing compartments have cooled sufficiently.

Yet still another object of the disclosed invention is to provide an electrical circuit for assuring user compliance with the necessary procedures for obtaining sterilized lenses and a sterilized bottle of rinse solution.

These and other objects and advantages of the invention will be readily apparent in view of the following description and drawings of the above described invention.

DESCRIPTION OF THE DRAWINGS

The above and other objects and advantages and novel features of the present invention will become apparent from the following detailed description of the preferred embodiment of the invention illustrated in the accompanying drawings, wherein:

FIG. 3 is a side elevational view with portions broken away of another embodiment of the invention of FIG. 1 and disclosing heat conductive material in the lid cooperating with the heat conducting and generating material in the apparatus base; and, FIG. 4 is a schematic block diagram of a circuit designed to operate the invention.

DESCRIPTION OF THE INVENTION

Figure 1:
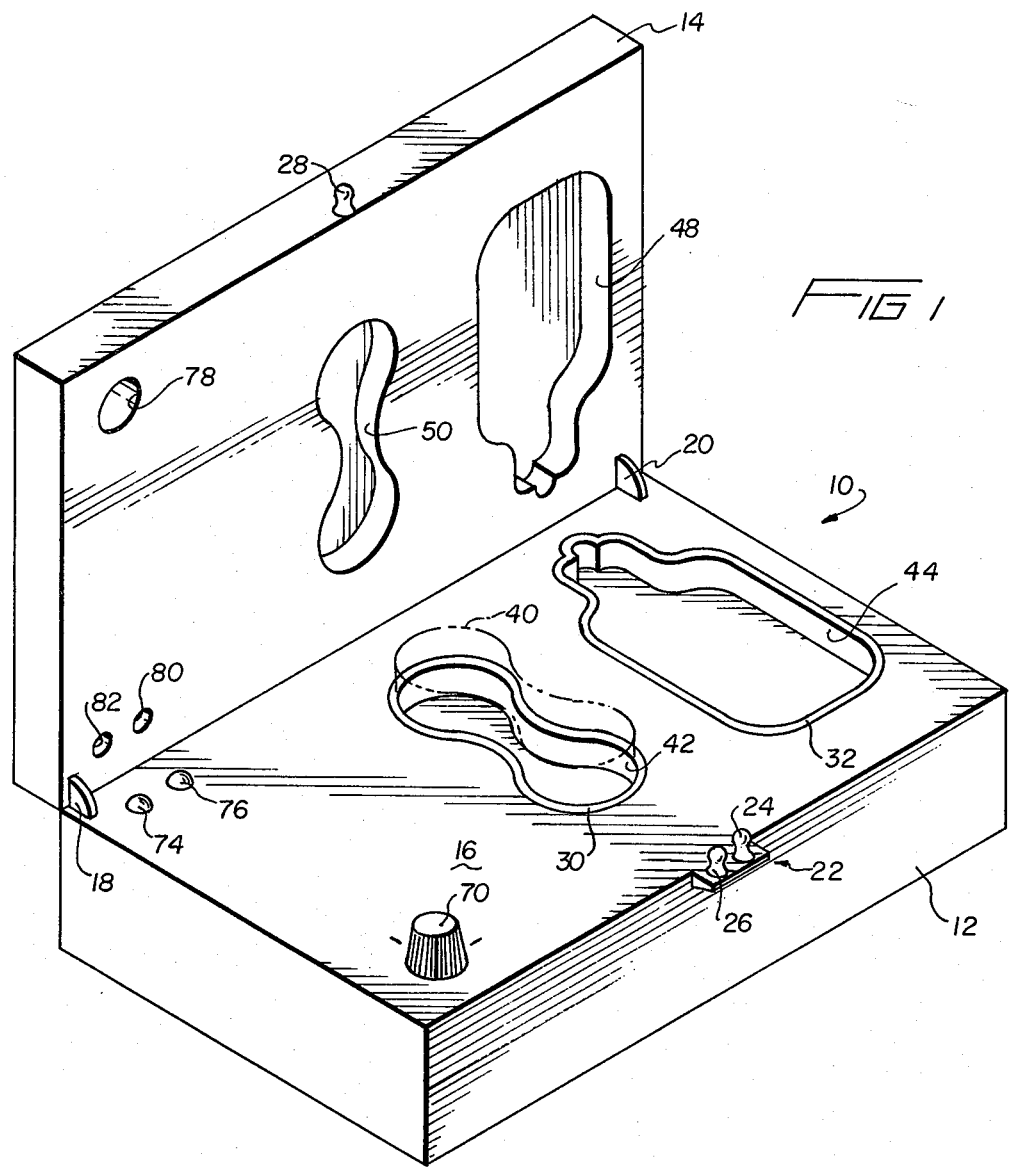
FIG. 1 is a perspective view of the apparatus of the invention and with the contact lens carrying case shown in phantom lines.

A fail safe sterilizer apparatus 10 as best shown in FIG. 1, includes a generally rectangular housing or base 12 and lid 14. Lid 14 is angularly displaceably mounted to upper surface 16 of housing 12 by means of cooperating hinges 18 and 20. Housing 12 includes catch 22 having cooperating uprights 24 and 26 adapted for securing therebetween member 28 depending from lid 14. In this way, lid 14 may be replaceably secured to housing 12.

Figure 2:
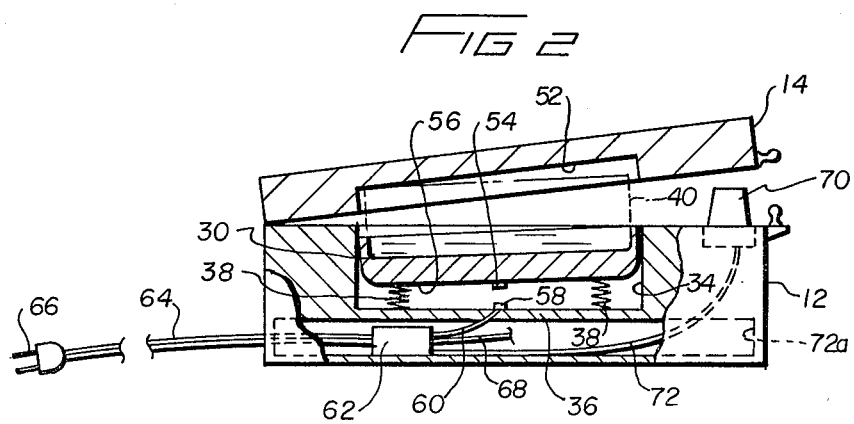
FIG. 2 is a side elevational view with portions broken away and portions shown in phantom lines and with the lid in the partially closed position.

Housing 12 includes at least two heat members 30 and 32 which are upwardly and downwardly displaceable in housing 12. Housing 12, as best shown in FIG. 2, includes a compartment or recess 34 for each heat member 30 and 32. Although only one recess 34 for heat member 30 is disclosed in FIG. 2, it should be obvious that a similar recess is also provided for heat member 32. Recess 34 includes a bottom support 36 from which springs 38 upwardly extend and similar springs and bottom support are supplied for the recess for heat member 32. Springs 38 support heat member 30, or heat member 32 as the case may be, and are adapted for reciprocally displacing heat member 30 in recess 34. Heat member 30 is, preferably, constructed of a heat conductive material, such as aluminum, and is adapted for generating heat by electrical current, as is well known in the art, so as to heat container 40 which is positioned in contoured recess 42 of heat member 30. It should be noted that contoured recess 42 is shaped so as to closely conform to the exterior of lens case or container 40. Similarly, contoured recess 44 of heat member 32 is contoured in the shape of a rinse solution bottle. The exact shape of contoured recesses 42 and 44 may be that of any shape which the lens case 40 assumes or which the rinse solution bottle (not shown) assumes. Those skilled in the art will appreciate that the shape of container 40 is a function of what is being contained. Heat members, such as heat members 30 and 32, are well known in the art and are fully described in Hoogesteger et al, U.S. Pat. No. 3,983,362, the disclosure of which is incorporated herein by reference.

Lid 14 includes contoured recesses 48 and 50 which are alignable with recesses 44 and 42, respectively, and which together define two sterilizing compartments when lid 14 is closed. As best shown in FIG. 2, when container 40 is positioned in recess 42 of heat member 30, and the lid 14 is closed, then the angular downward displacement of lid 14 causes container 40 to be pressed downwardly against springs 38 by upper surface 52 of recess 50 so as to permit member 28 to be secured between uprights 24 and 26. This downward displacement of heat member 30 causes contact 54 on bottom surface 56 thereof to engage or make electrical contact with contact 58 extending from bottom support 36. In the event that lid 14 is not fully closed or container 40 is not positioned in recess 42, then contact 54 will not connect with contact 58 and operation of the sterilizing apparatus 10 will not be available, as will be described herein later. It should be obvious, that a similar cooperating pair of contacts extends from heat member 32 and that, likewise, it is necessary that the rinse solution bottle (not shown) be positioned in recess 44 in order that the contacts of heat member 32 will also make electrical connection.

As best shown in FIG. 2, contact 58 is connected by cord 64 and plug 66 to a source of alternating current power. Additionally, line 68 which extends from control 62 is connected to the contact (not shown) of heat member 32. It should be obvious, that while alternating current power supply 64 and 66 is disclosed, that the use of dry cell batteries or other current supply means is also within the realm of use with the present invention.

As best shown in FIG. 1, on/off switch 70, of a type well known in the art, extends from upper surface 16 and is connected to control 62, as best shown in FIG. 2, by line 72. It should be noted, that control 62 and lines 60, 68 and 72 are positioned within a recess 72a. Electrically operable indicia 74 and 76, as best shown in FIG. 1, include light emitting diodes or other electrical illumination means and are adapted for indicating operation of or completion of operation of apparatus 10. Preferably, electrical indicia 74 and 76 each have their own separate distinct color, such as green and red, so as to be easily recognized by the user. Additionally, lid 14 includes apertures 78, 80 and 82 designed to permit access to switch 70 and viewing of electrically operable indicia 74 and 76. Preferably, control 62 includes means for causing flashing of indicia 74 and 76.

As best shown in FIG. 3, heat member 84, which is similar to heat members 30 and 32, and is provided with contact 85, has a cooperating contoured conductive member 86 disposed in recess 88 of lid 14. Cooperating member 86 is manufactured from a heat conductive material, such as aluminum, and is designed to further increase the heat transmission rate from heat member 84 to the container 90, which includes a rinse solution bottle, contained in heating or sterilizing receptacle 92 defined by heating member 84 and cooperating member 86. In this way, the heat transfer to container 90 is greatly increased. It should also be obvious, that a similar cooperating member could be cooperating with heat member 30 and 32 of FIG. 1. Similarly, contact 85 is adapted for making electrical connection with contact 87, for reasons to be explained later.

As best shown in FIG. 4, on/off switch 70, is connected to a source of alternating current (not shown) and to AC line fuse 96. Preferably line fuse 96 is approximately three amps, although the exact size thereof is dependent upon the configuration chosen. Fuse 96 is connected to direct current power source or rectifier 98. Power source 98 is adapted to convert alternating current to direct current and is preferably of an output of approximately 12 volts. Power supply 98 is in series connection with lid closure switches 100 and 102 which are similar to lid contacts 54 and 58 of heat member 30 as well as the contacts (not shown) for heat member 32. Lid contact switch 102 feeds parallel heating circuits 104 and 106.

Heating circuit 104 includes timing means 108, of which many types are well known in the art, and which is connected to lid closure switch 102. Relay 110 is connected to timing means 108 and is adapted for energizing resistance or heat member 112, which is similar to heat members 30 and 32. LED 74, is connected to timing means 108 and is adapted for indicating operation of resistance 112 when timing means 108 is activated. Ambient temperature sensing thermostat 116, of which many are known in the art, is connected to resistance or heat member 112 and is adapted for sensing the temperature and the contents of the container being heated therefore. Thermostat 116 may be of the normally opened or of the normally closed type.

Heating circuit 106 includes timing means 118 which is similar to timing means 108 but which does not, necessarily, have a time duration equal to that of timing means 108. Timing means 118 is connected to relay 120 which is connected to resistance or heat member 122. Resistance or heat member 122 is similar to heat members 30 and 32. Heat member or resistance 122 is connected to ambient temperature sensing thermostat 124 which is similar to thermostat 116. It is necessary that both thermostat 116 and thermostat 124 both be of the normally opened or normally closed type as they are connected to logic means or switching gate 126 which is adapted for comparing the output of thermostats 116 and 124. Switching gate 126 is of a type well known in the art and performs the function of logical inclusive OR. Switching gate 126 produces an output whenever both of its inputs, thermostats 116 and 124, are energized so as to drive the output of switching gate 126 into the "on" state. In this way a comparison may be made in order to ascertain that both resistances or heat members 112 and 122, which are similar to heat members 30 and 32, are at a temperature sufficiently cooled so as to permit wearing of the contact lenses or use of the rinse solution, both of which have been sterilized. Line 128 connects power source 98 to switching gate 126 in order to supply power to drive electrically operable LED 76. In this way, the user can be assured that the lenses and the rinse solution have been sufficiently cooled after having been sterilized so as to be worn.

OPERATION

The operation of fail safe sterilizer 10, which is operated according to the electrical circuit of FIG. 4, is relatively simple and yet assures that the contact lenses and the bottle of rinse solution are both simultaneously sterilized. The bottle of rinse solution is positioned in the appropriate heat member 32 and the lens case containing the pair of contact lenses is placed in the appropriate member 30 and the lid 14 is then closed. Closing of the lid 14 and securing of member 28 in latch 22 results in heat members 30 and 32 being depressed downwardly against the action of springs 38 so as to make contact with the switch contacts 54 and 58, extending upwardly from bottom support 36. After both lid closure switches, which are similar to lid closure switches 100 and 102 as well as to contacts 54 and 58, are made, then operation of on/off switch 70 permits current to flow from the AC power source to the rectifier where it is converted into direct current. It should be noted that if both recesses 42 and 44 are not occupied then both switches will not be made and the apparatus will not operate. The power supply 98 then feeds timing means 108 and 118 which energize relays 110 and 120, respectively, so as to cause resistances or heat members 112 and 122, respectively, to heat the containers 40 to the appropriate temperature.

At the present time, it is contemplated that a 25 watt resistance or heater such as resistances 112 and 122, would be sufficient to elevate the containers 40, and their contents, therefore, to a temperature of at least 85° C. This temperature is sufficient to attain disinfection but, however, the actual sterilizing temperature may be higher if desired. Timing means 108 and 118 are independent of each other but it is contemplated that both be capable of maintaining the 85° temperature for at least ten minutes. One of the timing means, for example timing means 108, could have a time duration in excess of that of the other timing means 118.

When the switch 70 is depressed and the lid closure switches 100 and 102 are both made, then the LED 74 is activated so that the user is aware that the sterilizing apparatus is in operation. It should be noted at this point, that should the user lift lid 14 while the heating function is still being performed, then the circuit would be opened and it would be necessary to completely restart the heating cycle.

After the timing means 108 and 118 have timed out, then the resistances 112 and 122, which are similar to heat members 30 and 32, begin to cool and this cooling is monitored by thermostats 116 and 124, respectively. Also, timing out of timing means 108 causes LED 74 to be extinguished. The thermostats 116 and 124 are set to monitor the temperature of the resistances 122 and 112 and are adapted to be tripped or otherwise send a signal to gate 126 when the temperature of the heating members 30 and 32, as represented by resistances 112 and 122, reaches a pre-selected temperature which is, preferably, ambient temperature or 25° C. The switching gate 126 senses that a signal is being received from both thermostats 116 and 124 and when both thermostats 116 and 124 indicate that ambient temperature has been achieved then the switching gate 126 signals LED 76 so that the user then knows that the cooling has been completed and that the contact lenses and the solution are ready for use. At that point, lid 14 may be raised and the LED 76 will be extinguished and the sterilizing apparatus 10 will be ready for another cycle.

While this invention has been described as having a preferred design, it is understood that it is capable of further modifications, uses and/or adaptations of the invention. Following in general the principals of the invention and including such departures from the present disclosure as come within known or customary practice in the art to which the invention pertains, and as may be applied to the central features herein before set forth, and fall within the scope of the invention to the limits of the appended claims.

What I claim is:
1. A fail safe sterilizing apparatus for simultaneously sterilizing lenses contained in a lens case and a bottle of rinse solution, comprising:
 (a) a housing comprised of a thermally insulating material and having a lid displaceable between an open and a closed position;
 (b) a pair of recesses disposed in said housing;
 (c) a first heat element displaceable mounted in a first one of said pair of recesses and including a first contoured recess therein for receiving a first container;
 (d) said first heat element includes a heat conductive element and electrically operable heating means for heating said first container;
 (e) a second heat element displaceably mounted in a second one of said pair of recesses and including a second contoured recess therein for receiving a second container;
 (f) said second heat element includes a heat conductive element and electrically operable heating means for heating said second container;

(g) said first and said second heat elements being displaced when said first and said second containers are positioned in said associate first and second contoured recesses and said lid is in said closed position;

(h) switch means are electrically connected with each of said first and second heat elements and are operable only when both said first and second heat elements have been displaced by said closed lid for thereby permitting operation of said associated heating means;

(i) a control means including an electrical control circuit is electrically connected with said switch means and each of said heating means for simultaneously energizing said heating means; and (j) means are electrically connected with said control means for connecting said control means to a source of electric power.

2. A sterilizing apparatus as defined in claim 1, wherein:
(a) said first recess being contoured in the shape of said lens case; and,
(b) said second recess being contoured in the shape of said bottle of rinse solution.

3. A sterilizing apparatus as defined in claim 1, wherein:
(a) spring means are disposed in said first and second pair of recesses for reciprocally supporting said first and second heat elements.

4. A sterilizing apparatus as defined in claim 3, wherein:
(a) each of said first and second pair of recesses including a bottom support; and,
(b) said spring means extending upwardly from said bottom support.

5. A sterilizing apparatus as defined in claim 4, wherein:
(a) said switch means including a switch means for each of said first and second heat elements; and,
(b) each of said switch means including a first contact secured to an associated heat element and a second contact engageable therewith secured to an associated bottom support.

6. A sterilizing apparatus as defined in claim 1, further comprising:
(a) indicia means operably electrically connected with said control means for indicating relative temperature of said heat elements.

7. A sterilizing apparatus as defined in claim 1, further comprising:
(a) first and second lid recesses aligned with said first and second heat elements when said lid is in said closed position for forming first and second sterilizing compartments therewith.

8. A sterilizing apparatus as defined in claim 7, wherein:
(a) each of said first and second lid recesses including auxiliary heat members.

9. A sterilizing apparatus as defined in claim 1, further comprising:
(a) said control means including timer means for independently controlling sterilizing duration of said first and second heat elements.

10. A sterilizing apparatus as defined in claim 1, further comprising:
(a) on/off switch means operably electrically connected with said control means.

11. A sterilizing apparatus as defined in claim 1, wherein:
(a) said housing including a chamber for positioning said control means therein.

12. In a sterilizing apparatus having in combination a housing of thermally insulating material and a lid, at least first and second heat elements disposed in said housing and operably associated with heat element switch means, a first contoured recess disposed in said first heat element for receiving a first contoured container, a second contoured recess disposed in said second heat element for receiving a second contoured container, said lid cooperating with said heat elements for defining at least first and second sterilizing compartments, the improvement comprising an electric heating system for said compartments, comprising:
(a) a pair of recesses disposed in said housing, each of said pair of recesses having one of said heat elements disposed therein;
(b) means are associated with said pair of recesses for displaceably supporting said heat elements;
(c) each of said heat elements includes a heat conductive element and electrically operable heating means for heating an associated one of said containers;
(d) said lid is pivotally connected to said housing and adapted for being pivoted between an open and a closed position;
(e) power supply means;
(f) first heat element switch means are electrically connected to said power supply means, said first heat element switch means being open when said lid is in said open position and being closed when said lid is in said closed position and said first contoured container is positioned in said first heat element contoured recess;
(g) second heat member switch means are electrically connected to said first heat element switch means, said second heat element switch means being open when said lid is in said open position and being closed when said lid is in said closed position and said second contoured container is positioned in said second heat element contoured recess;
(h) each of said heat elements is displaced for thereby closing said associated switch means by pivoting of said lid to said closed position when each of said contoured containers is positioned in an associated contoured heat element recess;
(i) first timing means are electrically connected to said second heat element switch means;
(j) said first heat element is electrically connected to said first timing means for heating said first contoured container to a preselected elevated temperature for a preselected time period;
(k) second timing means are electrically connected to said second heat element switch means;
(l) said second heat element is electrically connected to said second timing means for heating said second contoured container to a preselected elevated temperature for a second preselected time period; and,
(m) said first heat element and timing means and second heat element and timing means are electrically connected in parallel circuits whereby said first and second heat elements are only operable for energizing said associated heating means when both said first and second heat element switch means are closed.

13. An electric heating system as defined in claim 12, wherein:
   (a) said power supply means including rectifier means connectable to a source of alternating current.

14. An electric heating system as defined in claim 12, further comprising:
   (a) first relay means electrically connected to said first timing means and said first heat element for energizing said first heat element; and,
   (b) second relay means electrically connected to said second timing means and said second heat element for energizing said second heat element.

15. An electric heating system as defined in claim 12, further comprising:
   (a) electrically operable indicia means electrically connected to one of said first and second timing means for indicating operation of said first heat member.

16. An electric heating system as defined in claim 12, further comprising:
   (a) first thermostat means electrically connected to said first heat element and adapted for sensing said first heat element temperature;
   (b) second thermostat means electrically connected to said second heat element and adapted for sensing said second heat element temperature;
   (c) latch means electrically connected to said first and second thermostat means and adapted for transmitting current when said first and second thermostat means sense a pre-selected temperature; and,
   (d) electrically operable indicia means electrically connected to said latch means for indicating that said first and second heat elements have attained said preselected temperature.

17. An electric heating system as defined in claim 15, wherein:
   (a) said electrically operable indicia means including flashing means.

18. A fail safe sterilizing apparatus for simultaneously sterilizing lenses contained in a lens case and a bottle of rinse solution, comprising:
   (a) a housing comprised of a thermally insulating material and having a lid displaceable between an open and a closed position;
   (b) a pair of recesses disposed in said housing;
   (c) a first heat element displaceably mounted in a first one of said pair of recesses and including a first contoured recess therein for receiving a first container, said first recess being contoured in the shape of said lens case;
   (d) said first heat element includes a heat conductive element and electrically operable heating means for heating said first container;
   (e) a second heat element is displaceably mounted in a second one of said recesses and including a second contoured recess therein for receiving a second container, said second recess being contoured in the shape of said bottle of rinse solution;
   (f) said second heat element includes a heat conductive element and electrically operable heating means for heating said second container;
   (g) said first and said second heat elements being displaced when said first and second containers are positioned in said associated first and second contoured recesses and said lid is in said closed position;
   (h) switch means are electrically connected with each of said first and second heat elements and are operable only when said first and second heat elements have been displaced by said closed lid for thereby permitting operation of said associated heating means;
   (i) a control means including an electrical control circuit is electrically connected with said switch means and each of said heating means for simultaneously energizing said heating means; and
   (j) means are electrically connected with said control means for connecting said control means to a source of electric power.

* * * * *